United States Patent
Melius et al.

(10) Patent No.: US 11,565,105 B2
(45) Date of Patent: Jan. 31, 2023

(54) LEAD ANCHOR FOR A NEUROMODULATION LEAD

(71) Applicant: BIOTRONIK SE & CO. KG, Berlin (DE)

(72) Inventors: Matthew Melius, Portland, OR (US); Julia Khoury Valentine, Corvallis, OR (US); Eric Austin, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 136 days.

(21) Appl. No.: 16/593,230

(22) Filed: Oct. 4, 2019

(65) Prior Publication Data

US 2020/0108247 A1   Apr. 9, 2020

Related U.S. Application Data

(60) Provisional application No. 62/741,787, filed on Oct. 5, 2018.

(51) Int. Cl.
*A61N 1/05*   (2006.01)

(52) U.S. Cl.
CPC .................................. *A61N 1/0558* (2013.01)

(58) Field of Classification Search
CPC .......... A61N 1/0558; A61N 2001/0582; A61B 5/6882; A61B 5/6884
USPC ........................................................ 607/116
See application file for complete search history.

(56) References Cited

U.S. PATENT DOCUMENTS

| 5,476,493 | A  | * | 12/1995 | Muff ....................... | A61N 1/057 607/119 |
| 9,216,563 | B2 |   | 12/2015 | Barner | |
| 9,352,147 | B2 |   | 5/2016  | Nguyen-Stella et al. | |
| 9,433,755 | B2 |   | 9/2016  | Behymer et al. | |
| 2009/0171376 | A1 | * | 7/2009 | Burton ................... | A61M 25/04 606/151 |
| 2012/0185027 | A1 | * | 7/2012 | Pianca .................... | A61N 1/057 607/117 |
| 2012/0232626 | A1 | * | 9/2012 | Daglow ................ | A61N 1/3605 607/116 |
| 2012/0330354 | A1 | * | 12/2012 | Kane ........................ | A61N 1/05 606/232 |
| 2013/0204336 | A1 | * | 8/2013 | Sharma ................ | A61N 1/0558 607/117 |
| 2015/0112414 | A1 | * | 4/2015 | Conger ..................... | A61N 1/05 607/116 |
| 2015/0209574 | A1 | * | 7/2015 | Farhat .................... | B29C 39/026 607/116 |
| 2016/0001067 | A1 | * | 1/2016 | Pereira ..................... | A61L 24/00 607/116 |
| 2019/0209852 | A1 | * | 7/2019 | Nelson ................. | A61N 1/0558 |

* cited by examiner

*Primary Examiner* — Carl H Layno
*Assistant Examiner* — Jane C Kalinock
(74) *Attorney, Agent, or Firm* — Laurence A. Greenberg; Werner H. Stemer; Ralph E. Locher

(57) ABSTRACT

A lead anchor for a neuromodulation lead has an anchor body that receives a portion of the lead. A mesh is arranged so as to at least partially surround the portion of the lead when the portion of the lead is received in the anchor body.

12 Claims, 2 Drawing Sheets

LEAD ANCHOR FOR A NEUROMODULATION LEAD

CROSS-REFERENCE TO RELATED APPLICATION

This application claims the benefit, under 35 U.S.C. § 119(e), of provisional patent application No. 62/741,787, filed Oct. 5, 2018; the prior application is herewith incorporated by reference in its entirety.

BACKGROUND OF THE INVENTION

Field of the Invention

The instant invention generally relates to a lead anchor for a neuromodulation lead. In particular, the instant invention also relates to an implantable lead anchor being configured to reversibly clamp a spinal cord stimulation lead.

Neuromodulation consists of the delivery of electrical, magnetic, mechanical, thermal, or optical stimuli to the central or peripheral nervous system of a patient. To this end, an implantable medical device may be implanted in the patient's body, wherein the implantable medical device is configured for stimulating neural tissue, e.g., by means of one or more electrodes being arranged inside one or more leads.

A common example of such an implant-based neuro therapy is the spinal cord stimulation (SCS), in which case the implantable medical device comprises an implantable pulse generator (IPG) and typically two leads. The leads extend along the spinal cord and have a plurality of electrodes (for example eight electrodes per lead) that couple to the neural tissue at different locations in the spinal cord.

SCS is an emerging technique for providing long-term pain relief to a patient as an alternative to medication in cases where corrective surgery is no longer an option. The effectiveness of SCS is dependent upon the positioning of two sets of electrodes at the end of conductive leads within the spinal column. The location of the electrodes relative to each other and the spinal cord is paramount to successful therapy. During normal patient activity, the leads will experience stresses that can cause the leads to migrate. Migration of a lead may result in an unwanted change or loss of therapy, requiring a corrective action.

The problem presented by lead migration is conventionally addressed through the application of an anchoring device that is designed to secure the lead to the fascia at the point where the lead enters into the spinal column. For example, to ensure that the leads do not move once they have been placed, such an anchoring device may be placed along a portion of the lead.

A traditional "passive" lead anchoring system is most often comprised of a silicone body which has a hollow cylindrical portion (which may also be referred to as lumen) where the lead is passed through. There are often eyelets provided on the anchor so that it can be fixed in place with sutures. The traditional anchors are typically employed to keep the leads in a relatively secure position. However, they do not provide resistance to axial forces, which in the case of SCS lead is the main cause of lead migration. It is for this reason desirable that anchors are designed to have an activated locking mechanism specifically to prevent axial motion of the leads.

Further, the initial positioning of each lead is subject to change during the initial operation and during the lifetime of the therapy. It is therefore desirable that the anchoring system has the ability to unlock, reposition and relock at the physicians' discretion.

Active lead anchor solutions that are currently available utilize semi-permanent locking mechanisms. Some are irreversible, using, e.g., adhesive to fix the anchor to a lead for ensuring that the lead position does not change once the anchor is placed. For example, the U.S. Pat. No. 9,216,563 B2 proposes an adhesive-based solution.

Other solutions have snapping mechanisms which 'click' into place through twisting or pinching a portion of the lead anchor relative to another portion of the lead anchor. These solutions are hand actuated and do not require unique tools to manipulate.

A few solutions exist where a set screw is articulated and the lead is compressed under the screw tip by either the screw itself or by a protective polymer sleeve or pressure plate.

Due to the relative complexity and unique designs associated with the lead system, most of the existing anchor solutions are unique to the lead that they are designed to secure.

The existing lead anchor concepts mentioned above have the following drawbacks:

Anchors which require adhesion are challenging in the case where the lead would require adjustment for improved therapy. In that case, the anchor would have to be cut from the lead and a new anchor would then have to be placed along the lead at a new position.

Further, some known solutions may require a special handling tool that is used specifically with the anchor and has no other function to a physician. For example, the U.S. Pat. No. 9,433,755 B2 describes a dedicated anchor deployment assembly. Such tools may require additional training to ensure proper usage. In the case of removal and replacement the risk of lead migration may be significant.

The solutions that use 'clicking' or hand actuated mechanisms run the risk of patient actuation during the lifetime of the device. This could occur without the patient being aware and would likely result in lead migration and ultimately a corrective operation. Additionally, the hand actuation usually requires that the lead anchor be free from tissue and presents a risk of causing the electrodes to move under the actuation force of the locking mechanism.

There are embodiments that utilize set screw to compress the lead body or a protective sleeve around the lead. For example, the U.S. Pat. No. 9,352,147 B2 discloses a lead anchor comprising a sleeve that is deformable by a fastener so as to obstruct a lead lumen and keep a lead body that is arranged therein in place.

Generally, the technique of manipulating the lead under the action of a set screw must be carefully considered. If unrestrained, contact between the set screw and the lead may cause damage to the lead resulting in the loss of its ability to provide therapy. For example, the lead system may be irreversibly (i.e., permanently) changed under the influence of the set screw. As a result, once the anchor is actuated, removal of the anchor may require replacement of the lead.

BRIEF SUMMARY OF THE INVENTION

It is an object of the present invention to provide an improved lead anchor, which overcomes the drawbacks of known solutions. In particular, due to the relative complexity and fragility of the lead, it is desirable for an anchor to be able to secure the lead in place without causing undue stress to the lead body while performing its desired function. For example, it is desirable to eliminate the risk of irreversible effects on the lead system or unintentional unlocking of the lead anchor.

With the above and other objects in view there is provided, in accordance with the invention, a lead anchor for a neuromodulation lead, which comprises an anchor body that is configured to receive a portion of the lead, and a mesh that is arranged so as to at least partially surround the portion of the lead when the portion of the lead is received in the anchor body. The mesh may comprise (or, consist of) a metal.

For example, the mesh may be arranged in contact with said portion of the lead. Hence, a material interface in the form of said mesh may be arranged within the lead anchor. The material interface may provide distributed contacts along the lead body. Thus, friction between the lead and the anchor may be increased, thereby providing grip to resist axial forces and preventing lead migration. In other words, the mesh may enable a distributed loading of the lead body, thus preventing acute mechanical damage. Due to the fact that the interface material is provided in the form of a mesh, adequate flexibility and grip on the lead may be advantageously combined.

For example, the mesh may be compressible. Thus, the required flexibility to conform to complex internal lead geometries may be provided.

In an embodiment, the mesh is reversibly (e.g., elastically) deformable. For example, the mesh may return to its original form when a locking mechanism of the lead anchor is released.

In an embodiment, the mesh has a shape memory function and/or comprises an elastic material. For example, the mesh may comprise or consist of a material such as, e g., nitinol. Nitinol is highly flexible under stress, but when released from a loading condition will return to its original shape. The inclusion of a compressible mesh made from memory metal may provide a fully reversible lead anchor solution. This functionality provides direct advantages including reversibility and flexibility over the expected lifetime of the implantable medical device.

According to an embodiment, the lead anchor comprises a clamping element, which may in turn comprise the mesh. Thus, the clamping element may be configured to reversibly clamp a portion of the lead by means of a reversible deformation of the mesh. For example, the clamping of the lead (via the mesh) may hinder an axial displacement of the lead relative to the anchor body of the lead anchor. With such a solution, the process of securing the lead may be reversible over the lifetime of the anchor so that if the therapeutic system needs change, the lead position can be adjusted without removal of the lead or anchoring system entirely.

In an embodiment, the clamping element comprises an actuator being configured to reversibly activate the clamping function of the clamping element. For example, the actuator may be configured to induce a reversible deformation of the mesh. The ability to reverse the locking mechanism of the lead anchor provides flexibility to the implantation procedure and facilitates lead repositioning. To ensure that the lead is not damaged by the activation mechanism (i.e., the actuator), said material interface in the form of the mesh may be included within the anchor, which will compress and conform to the outer surface of the lead body without constricting the conductors within the lead body. The reversibility of the anchoring system may remove any risk of damaging the lead during removal of the anchor or migration of the lead during activation or deactivation which could occur in the semi-permanent and hand actuated solutions.

In a variant of the embodiment mentioned above, the actuator is or comprises a set screw, which may impinge, e.g., on the mesh. For example, the set screw may be activated by means of a torque wrench. Set screws and torque wrenches are common tools used in connecting leads to implantable pulse generators and are hence generally available in the field. A set screw actuator may thus reduce the need for an additional tool and special training which is generally required in the case of solutions which utilize custom staples, or other mechanisms.

For example, the set screw activation may 'lock' the lead into place by creating contact with the lead. According to the present invention, for example, the compressible mesh may be included between the set screw and the lead body so as to avoid damage to the lead. The set screw may thus provide a secure locking mechanism that cannot be unlocked without direct articulation of the screw using a torque wrench.

For example, in a further variant embodiment, the lead anchor may be designed specifically to accommodate a custom magnetic resonance imaging (MRI) compatible lead. Such an MRI lead may have sections that are fundamentally different in contour and rigidity from usual SCS leads. The discontinuous nature of the MRI lead provides an additional complexity to the solution requirements. For example, the engagement with the anchor during activation must be flexible enough to constrict rigid and soft portions of a SCS lead without losing its functionality in either case.

According to an embodiment, the clamping element is configured as a C-clamp. Accordingly, for example, the clamping element may comprise a C-clamp body, wherein the mesh may form at least a part of a C-shaped lead support portion of the C-clamp body. For example, the mesh may have a C-shaped cross-section.

In an embodiment in accordance with the above-mentioned variant, an actuated set screw as described above may impinge on a portion of the C-clamp, such as directly on the mesh.

According to another variant embodiment, the mesh forms a sleeve being configured to receive a portion of the lead. For example, in accordance with this variant, the lead anchor may comprise a set screw collar (forming, e.g., a part of a clamping element as described above), wherein the sleeve may be at least partially arranged inside the set screw collar. In other words, the sleeve-shaped mesh may be arranged as an inlay inside the set screw collar.

The anchor body may define a lumen for receiving a portion of the neuromodulation lead. For example, the anchor body may comprise (e.g., consist of) silicone. Further, it may be provided that the anchor body has at least one fastener portion, e.g., in the form of one or more eyelets. The fastener portion(s) may be configured for fastening the anchor body to the tissue of a patient. For example, the fastener portions may be attached to the fascia of the patient, e.g., by means of a suture.

Summarizing, in accordance with the present invention, a fully reversible, set screw activated lead anchor for spinal cord stimulation system may be provided. By using a mesh, which may be formed, e.g., of a shape memory metal, the present invention enables a lead anchoring mechanism that provides adequate retention forces on a (potentially discontinuous) lead body while reducing the complexity of an operating procedure.

Other features which are considered as characteristic for the invention are set forth in the appended claims.

Although the invention is illustrated and described herein as embodied in a lead anchor for a neuromodulation lead, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

Like reference numerals designate like structural elements throughout the figures of the drawing. Further, it will be noted that the illustrated embodiments are not limiting for the invention, but they merely represent illustrative examples.

DETAILED DESCRIPTION OF THE INVENTION

Figure 1A:
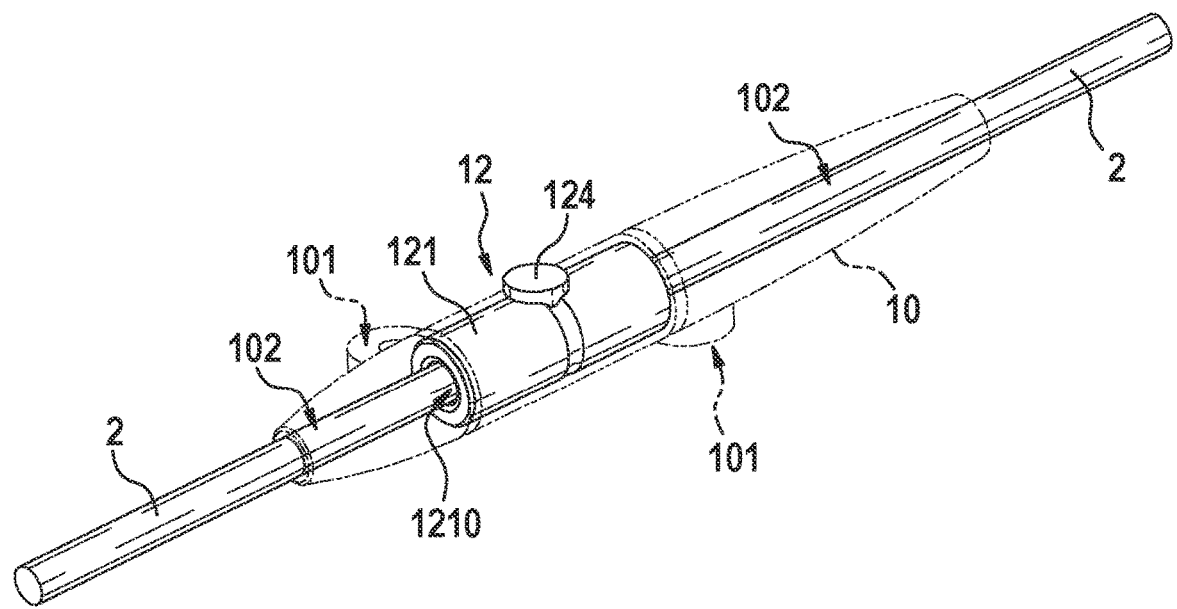
FIG. 1A is a schematic perspective view of an exemplary lead anchor according to one or more embodiments of the invention.

Referring now to the figures of the drawing in detail and first, particularly, to FIG. 1A thereof, there is shown a schematic and exemplary perspective view of a lead anchor 1 for a neuromodulation lead 2 in accordance with one or more embodiments. More precisely, an arrangement of a lead 2 and a lead anchor 1 is shown in a state wherein the lead 2 is secured to the lead anchor 1.

The lead anchor 1 has an elongate anchor body 10, which may, for example, comprise or consist of silicone. For the purpose of illustration, the anchor body is depicted transparent in FIG. 1A. That is, while the contours of the anchor body 10 are shown, structures that are arranged inside the anchor body 10 are also illustrated.

The anchor body 10 defines a lumen 102 that is configured for receiving a portion of the lead 2. Further, the anchor body 10 has fastener portions 101 in the form of eyelets for fastening the anchor body 10 to a patient's tissue (e.g., fascia) by means of a suture. For example, the lead anchor device may thus be configured to secure the lead 2 to the fascia at the point where the lead enters into the spinal column.

The illustrated lead anchor 1 is equipped with an active anchor locking mechanism which allows for locking the lead 2 inside the anchor body 10. This is to say that the locking mechanism of the lead anchor 1 may be activated to prevent axial motion of the leads relative to the anchor body 10. To this end, a clamping element 12 of the lead anchor 1 is provided.

In the exemplary embodiment shown in FIG. 1A, the clamping element 12 comprises a set screw collar 121 and an associated set screw 124. The set screw collar 121 defines a lumen 1210, which is axially aligned with the lumen 102 of the anchor body 10, such that the lead 2 may extend through the lumen 102 of the anchor body 10 as well as through the lumen 1210 of the set screw collar 121, as illustrated.

The set screw 124 may be (reversibly) activated, e.g., by means of a torque wrench, to clamp the portion of the lead 2 extending inside the lumen 1210 of the set screw collar 121. In other words, the set screw 124 serves as an actuator that is configured to reversibly activate the clamping function of the clamping element 12. The clamping mechanism of the clamping element 12 will be explained in some more detail in the following with reference to FIG. 1B.

Figure 1B:
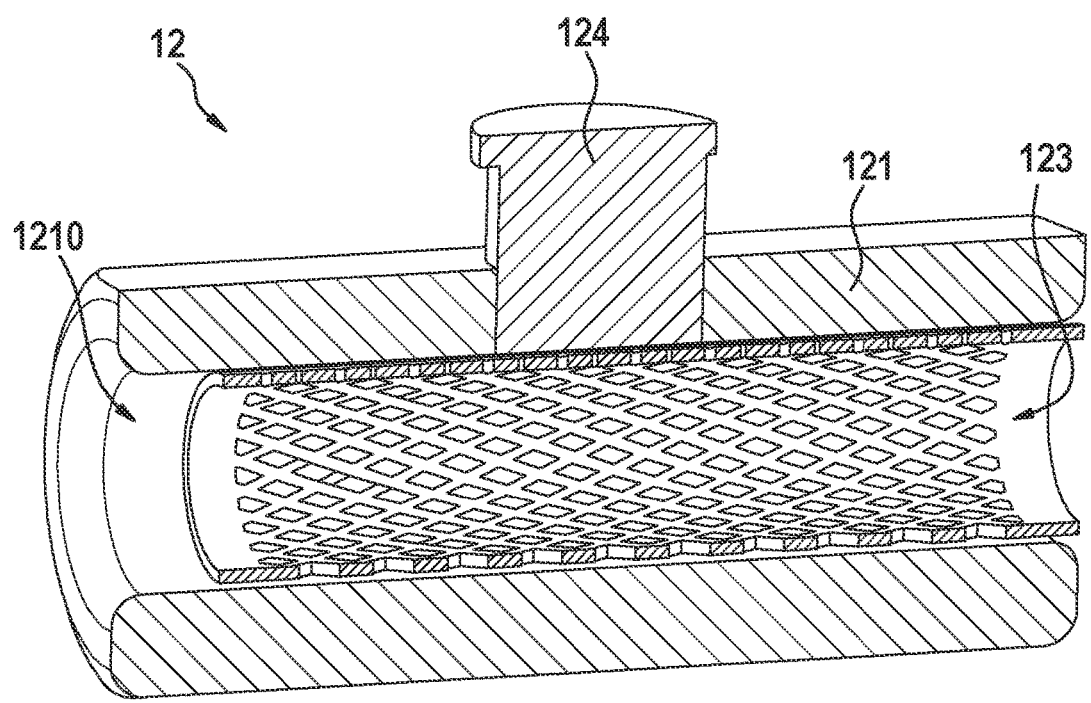
FIG. 1B is a schematic longitudinal cross-section through a clamping element of the lead anchor of FIG. 1A.

FIG. 1B shows a longitudinal (i.e., axial) cross-section through the clamping element 12 of the lead anchor 1 of FIG. 1A. The cross-section shows the set crew collar 1210 including its lumen 1210, as well as the set screw 124.

Further, the cross-sectional view in FIG. 1B reveals that the clamping element 12 comprises a mesh 123 in the form of a sleeve. The sleeve 123 is arranged as an inlay inside the lumen 1210 of the set screw collar 121, such that a portion of the lead 2 may extend through the sleeve 123. In other words, the mesh 123 may (at least partially) surround the portion of the lead 2 when the latter extends inside the anchor body 10. Further, in that case, the mesh 123 may be arranged in direct contact with the portion of the lead 2.

By way of example, the mesh 123 may comprise or consist of a metal, e.g., a shape memory metal such as nitinol.

Further, the mesh 123 may be compressible, such that it compresses under the force of the set screw 124. In this way, the force exerted on the compressible mesh 123 may be distributed along the lead body 2 so as to eliminate the possibility of damaging the lead body 2 or conductors that may be arranged therein. Hence, the clamping element 12 may be configured to reversibly clamp a portion of the lead body 2 by means of a reversible deformation of the mesh 123, which is induced by the activation of the set screw 124. Thereby, the mechanical force exerted by the set screw 124 may be distributed over the whole mesh area of the mesh 123.

The geometric mesh pattern is advantageous because it creates stress relief points along the surface of the lead body 2. This may allow portions of an outer tubing (consisting, e.g., of polyethylene) of the lead body 2 to fill in the gaps in the mesh 123. This may further reduce stress on the lead conductors and increase the anchor's 1 grip on the lead body 2.

The use of a metal mesh 123 having a shape memory function has the advantage that the mesh 123 can withstand high levels of stress and will return to its original uncompressed state once the set screw 124 is no longer pressing on the mesh 123. This provides a highly reversible lead anchor solution, allowing placement and removal of the lead anchor 1 during the entire operational life time of the lead anchor 1.

Figure 2A:
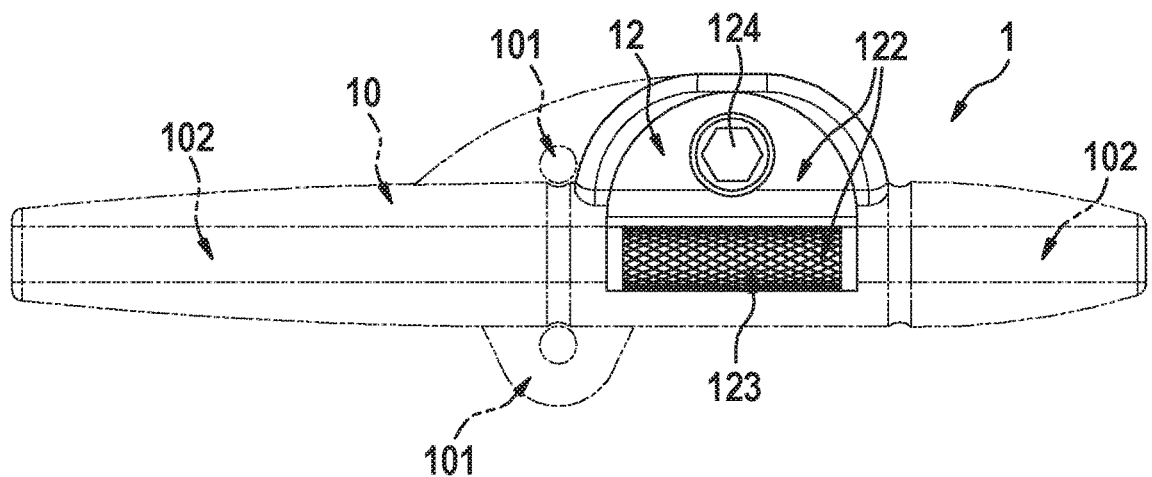
FIG. 2A is a schematic side view of an exemplary lead anchor in accordance with one or more further embodiments of the invention.
Figure 2B:
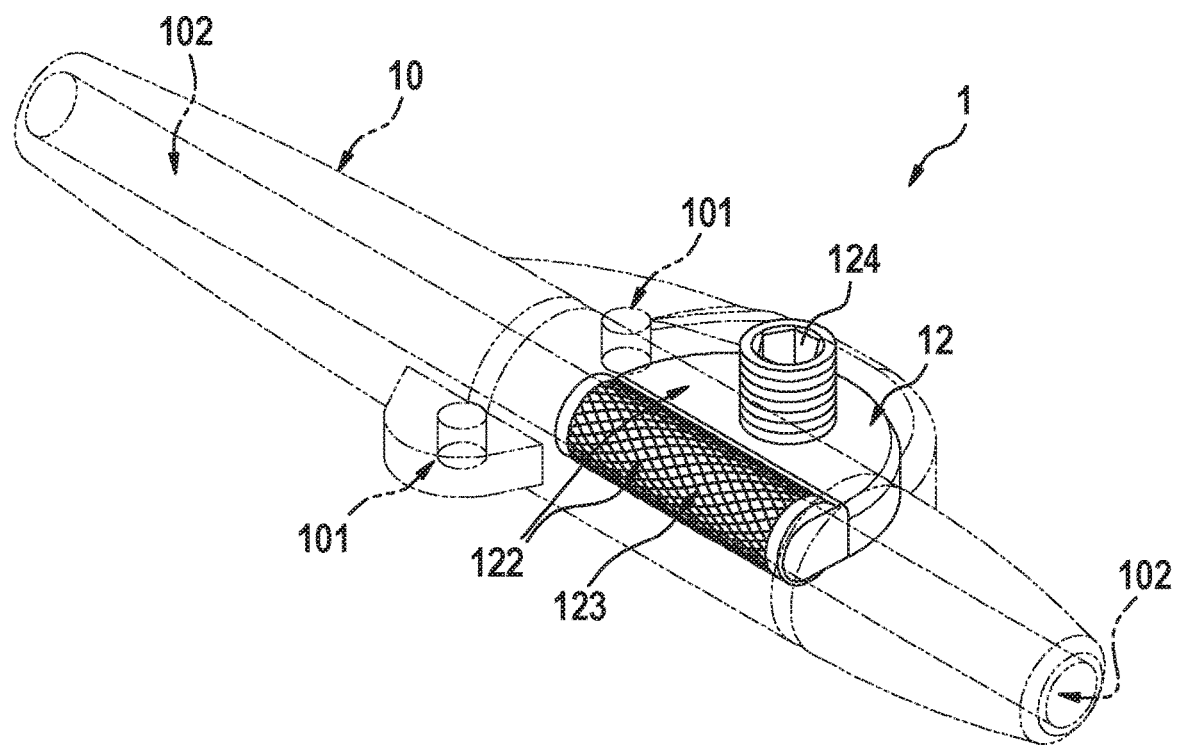
FIG. 2B illustrates a perspective view of the lead anchor of FIG. 2A.

FIG. 2A is a schematic and exemplary side view of a lead anchor 1 in accordance with one or more further embodiments. FIG. 2B schematically and exemplarily illustrates a perspective view of the lead anchor 1 of FIG. 2A. In the following, reference will be made to both FIG. 2A and FIG. 2B.

In the exemplary embodiments of FIGS. 2A and 2B, the anchor body 10 if the lead anchor 1 is similar to the anchor body 10 described above with reference to FIGS. 1A and 1B.

The embodiment of FIGS. 2A and 2B differs from the one of FIGS. 1A and 1B in that the clamping element 12 of the activated lead anchor 1 is configured as a C-clamp. An actuator 124 in the form of a set screw is configured to (reversibly) compress two flanges of a C-clamp body 122. Thus, a portion of a lead body 2 extending through a C-shaped lead support of the C-clamp body 122 may be clamped (i.e., 'locked').

In the exemplary embodiment of FIGS. 2A-B, the C-shaped lead support section of the C-clamp body 122 is provided in the form of a mesh 123. Accordingly, in this embodiment, the mesh 123 may have a C-shaped cross-section.

For more details and properties of the mesh 123, e.g., with regard to possible materials, it is referred to the above description in connection with FIGS. 1A-B. The mesh 123 of the present embodiment may have analogous advantages as the ones described above. For example, as explained earlier with reference to FIGS. 1A-B, when the C-shaped lead support (i.e., the mesh 123) compresses under the action of the set screw 124, the mesh 123 may advantageously provide a distributed compression along the lead body 2 without damaging the lead conductors.

In principle, however, the C-shaped lead support may consist of any suitable material, i.e., not necessarily of a mesh 123. For example, the C-shaped lead support could be made of a memory metal or another flexible material providing sufficient reversibility, wherein the C-shaped lead support may not necessarily have a mesh-shape.

It is also conceivable that a mesh 123 as described above be provided additionally as an inlay inside a C-shaped lead support. For example, in this case, the inlay mesh may be provided as a sleeve 123, as described above with reference to FIG. 1B. Alternatively, such an inlay mesh may have a C-shaped cross-section, for example.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The following is a summary list of reference numerals and the corresponding structure used in the above description of the invention:

1 Lead anchor
10 Anchor body
101 Fastener portion
102 Lumen of the anchor body
12 Clamping element
121 Set screw collar
1210 Lumen of the set screw collar
122 C-clamp body
123 Mesh
124 Actuator
2 Lead body

The invention claimed is:

1. A lead anchor for a neuromodulation lead, the lead anchor comprising:
an anchor body configured to receive a portion of the neuro-modulation lead;
a compressible mesh disposed to at least partially surround the portion of the neuromodulation lead when the portion of the neuromodulation lead is received in the anchor body, said compressible mesh being arranged in contact with said portion of the neuromodulation lead;
a clamping element containing said mesh, said clamping element being configured for reversibly clamping a portion of the neuromodulation lead by way of a reversible deformation of said compressible mesh, said clamping element including an actuator configured to reversibly activate a clamping function of said clamping element; and
said actuator is or includes a set screw.

2. The lead anchor according to claim 1, wherein the compressible mesh comprises a metal.

3. The lead anchor according to claim 1, wherein the compressible mesh has a shape memory function.

4. The lead anchor according to claim 1, wherein the compressible mesh comprises nitinol.

5. The lead anchor according to claim 1, wherein said clamping element is a C-clamp.

6. The lead anchor according to claim 5, wherein said clamping element comprises a C-clamp body, and said compressible mesh forms at least a part of a C-shaped lead support portion of said C-clamp body.

7. The lead anchor according to claim 1, wherein said compressible mesh has a C-shaped cross-section.

8. The lead anchor according to claim 1, wherein said compressible mesh forms a sleeve that is configured to receive the portion of the neuromodulation lead.

9. The lead anchor according to claim 8, further comprising a set screw collar, wherein said sleeve is at least partially arranged inside said set screw collar.

10. The lead anchor according to claim 1, wherein said anchor body defines a lumen for receiving the portion of the neuromodulation lead.

11. The lead anchor according to claim 1, wherein said anchor body has at least one fastener portion configured to fasten said anchor body to tissue of a patient.

12. A lead anchor for a neuromodulation lead, the lead anchor comprising:
an anchor body configured to receive a portion of the neuro-modulation lead;
a compressible mesh disposed to at least partially surround the portion of the neuromodulation lead when the portion of the neuromodulation lead is received in the anchor body, said compressible mesh being arranged in contact with said portion of the neuromodulation lead;
a clamping element containing said compressible mesh; and
said clamping element including a set screw arranged to directly or indirectly reversibly clamp a portion of the neuromodulation lead in said anchor body by way of a reversible deformation of said compressible mesh.

\* \* \* \* \*